United States Patent

Matsui et al.

[11] 3,939,202
[45] Feb. 17, 1976

[54] PROCESS FOR PREPARING POLYENE COMPOUNDS

[75] Inventors: Masanao Matsui, Tokyo; Seiichi Kitamura, Ibaraki; Masahiro Morioka, Suita, all of Japan

[73] Assignee: Teikoku Chemical Industry Co., Ltd., Osaka, Japan

[22] Filed: Jan. 29, 1974

[21] Appl. No.: 437,557

[30] Foreign Application Priority Data
Jan. 31, 1973 Japan.............................. 48-12566
June 15, 1973 Japan.............................. 48-67566
June 15, 1973 Japan.............................. 48-67567

[52] U.S. Cl......... 260/489; 260/405.5; 260/465.8 R; 260/476 R; 260/479 R; 260/479 S; 260/483; 260/484 P; 260/485 R; 260/488 H; 260/535 P; 260/537 N; 260/546; 260/561 K; 260/561 N; 260/614 R; 260/631.5
[51] Int. Cl.²......................................... C07C 67/00
[58] Field of Search............. 260/488 H, 489, 631.5, 260/682, 614 R, 476 R, 405.5, 537 N, 485 R, 479 R, 465.8 R, 546, 561 N

[56] References Cited
OTHER PUBLICATIONS
Wagner et al., *Synthetic Organic Chemistry*, John Wiley & Sons Inc. (New York) 1953, pp. 32 and 149.
Fieser et al., *Advanced Organic Chemistry*, Reinhold Publishing Corp. (New York), 1961, p. 140.

*Primary Examiner*—Richard L. Raymond
*Attorney, Agent, or Firm*—Jones, Tullar & Cooper

[57] ABSTRACT

Polyene compounds of the formula:

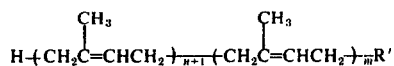

wherein R' is protected or unprotected hydroxyl or a group of the formula:

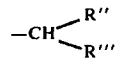

(in which R'' and R''' are each carboxyl or a group convertible into carboxyl on hydrolysis), $m$ is a positive integer and $n$ is 0 or a positive integer, which are useful as intermediates in the synthesis of coenzyme Q, can be produced advantageously through a step for the dehydration of a compound of the formula:

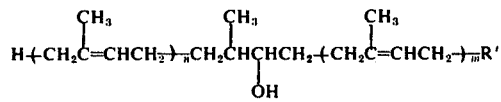

wherein R', $m$ and $n$ are each as defined above.

9 Claims, No Drawings

PROCESS FOR PREPARING POLYENE COMPOUNDS

The present invention relates to a process for preparing polyene compounds. More particularly, it relates to an industrially advantageous process for production of polyene compounds which form the side chains in a variety of natural products having a great number of carbon atoms as coenzyme Q.

Coenzyme Q is well known to have pharamacological activities on the nervous system of mammals including human beings. Particularly, the one having a side chain of 40 to 50 carbon atoms exhibits a remarkable pharamological effect. Such coenzyme Q (e.g. coenzyme $Q_8$, coenzyme $Q_{10}$) has heretofore been obtained by extraction from natural sources or by some synthetic or semi-synthetic methods [cf. Crane et al.: *Biohim. Biophys. Acta*, 25, 200 (1957); Lester et al.: *J. Am. Chem. Soc.*, 80, 4751 (1958); Shunk et al.: *J. Am. Chem. Soc.*, 81, 5000 (1959); Obolnikova et al.: Zhur. Obshch. Khim., 34, 1499 (1964), etc.]. However, none of them is satisfactory for the industrial production of coenzyme Q. In case of extraction from natural sources, the contents of coenzyme Q in the known sources are entirely small so that an enormous amount of the sources is needed. On the other hand, the bottleneck in any semi-synthetic or synthetic method is the difficult production of the polyene side chains. When the polyene side chains are attempted to obtain from plant sources, the separation of the compounds having a certain length of polyene side chain requires a tedious operation. In addition, their contents in the plant sources are extremely small. When the polyene side chains are tried to obtain by totally synthetic methods, the yields are generally low. Moreover, the produced polyene compounds are a mixture of cis- and trans-isomers, and the elimination of the ineffective cis-isomers and the recovery of the effective trans-isomers from such mixture are very difficult.

As the result of the extensive study, there has now been established a process for preparing polyene compounds which are useful as intermediates in the synthesis of coenzyme Q. It is notable that the process can predominantly afford polyene compounds in the trans form. It is also notable that the process can give the polyene compounds having an optional number of carbon atoms.

The process of this invention is representable by the following scheme:

Scheme I

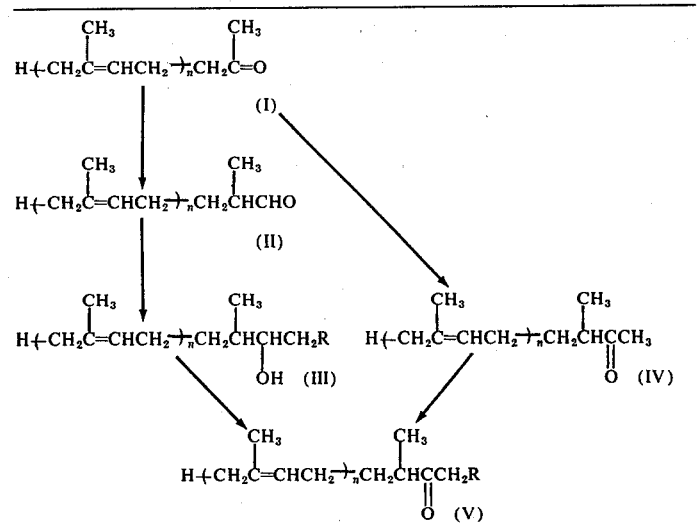

Scheme II

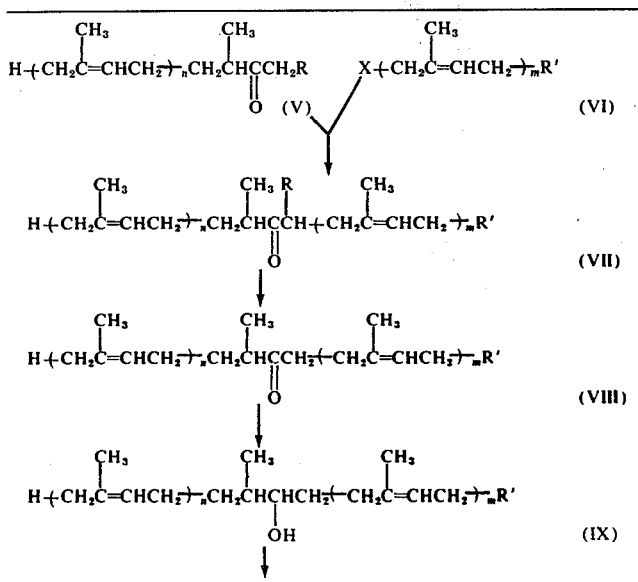

Scheme II-continued

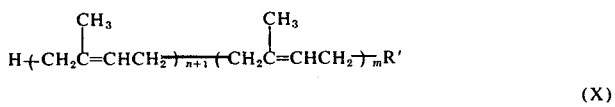

(X)

wherein R is a group convertible into carboxyl on hydrolysis, R' is protected or unprotected hydroxyl or a group of the formula:

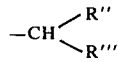

(in which R'' and R''' are each carboxyl or a group convertible into carboxyl on hydrolysis), X is the residue of an acid, m is a positive integer and n is 0 or a positive integer.

In the above definitions, the residue of an acid represented by the symbol X may be halogen (e.g. chlorine, bromine), lower alkanesulfonyloxy (e.g. methanesulfonyloxy), arenesulfonyloxy (e.g. benzenesulfonyloxy, toluenesulfonyloxy) or the like. As the group convertible into carboxyl, there may be exemplified alkoxycarbonyl (e.g. methoxycarbonyl, ethoxycarbonyl, propoxycarbonyl, isopropoxycarbonyl, butoxycarbonyl, pentoxycarbonyl, hexyloxycarbonyl), aryloxycarbonyl (e.g. phenoxycarbonyl, tolyloxycarbonyl, naphthyloxycarbonyl), cyano, carbamoyl, alkanoyloxycarbonyl (e.g. acetoxycarbony, butyryloxycarbonyl), aroyloxycarbonyl (e.g. benzoyloxycarbonyl), etc. The protected hydroxyl group may be, for instance, alkoxy (e.g. methoxy, ethoxy, propoxy), alkanoyloxy (e.g. acetyloxy, butryloxy), aroyloxy (e.g. benzoyloxy, p-methylbenzoyloxy) or the like. As to m and n, no upper limit is present, but they may be usually not more than 10.

Making reference to the above scheme, the process of this invention will be hereinafter illustrated in details step by step.

In the first step, the compound (I) is reacted with a carboxylic acid derivative of the formula: RCH₂X in which R and X are each as defined above, followed by hydrolysis and decarboxylation. The conversions in this step are representable by the following formulae:

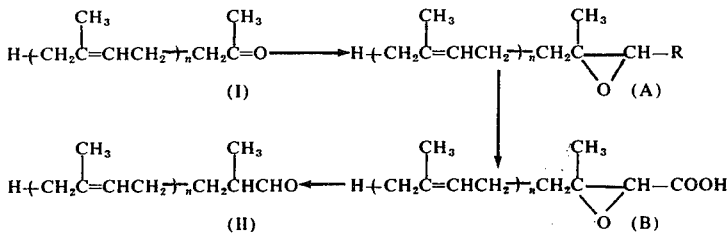

wherein R and n are each as defined above.

The reaction with the carboxylic acid derivative is usually carried out in the presence of a basic catalyst such as an alkali metal alkoxide (e.g. sodium methoxide, sodium ethoxide), an alkali metal hydride (e.g. sodium hydride, lithium hydride) or an alkali metal amide (e.g. sodium amide, potassium amide), preferably under an inert gas atmosphere (e.g. nitrogen, helium) at a temperature of from −30° to 15°C. The product (A) may be subjected to hydrolysis with or without its previous separation from the reaction mixture. Hydrolysis may be effected in a per se conventional manner, e.g. by treatment with an acid or a base. The use of a base is generally preferred. Thus, the hydrolysis is normally performed by treatment with an alkali metal hydroxide or an alkaline earth metal hydroxide in a lower alkanol (e.g. methanol, ethanol) at a wide range of temperature, for instance, while cooling with ice, at room temperature or under refluxing. The resultant carboxylic acid (B) is then subjected to decarboxylation by a per se conventional manner, e.g. heating at a temperature of from 100° to 200°C preferably under reduced pressure. Prior to the decarboxylation, the separation of the carboxylic acid from the reaction mixture, for instance, by extracting with an organic solvent (e.g. ether, xylene, toluene) under an acidic condition is favorable.

In the second step, the thus prepared compound (II) is reacted with a carboxlic acid derivative of the formula: RCH₂X in which R and X are each as defined above to give the compound (III). The reaction is usually carried out in an inert solvent (e.g. ether, tetrahydrofuran, dioxane, benzene, toluene, xylene) in the presence of a metal catalyst (e.g. metallic zinc, metallic magnesium) at a wide range of temperature from cooling with ice to reflux. The intermediate present in the reaction mixture at this stage is presumed to have the following formula:

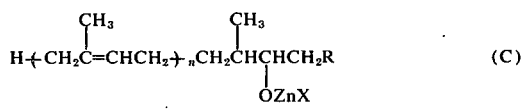

(C)

wherein R, X and n are each as defined above. Treatment of the reaction mixture with water or, preferably, an acid solution (e.g. 5 to 10% hydrochloric acid, 5 to 10% sulfuric acid) affords the compound (III).

In the third step, the compound (III) is subjected to oxidation to give the compound (V). The oxidation may be carried out in a per se conventional manner as empolyed for the oxidation of a secondary hydroxyl group. For instance, the treatment with an oxidizing agent such as manganese oxide, potassium permanganate, chromic acid, chromic acid-sulfuric acid, chromic acid-pyridine or phosphorous pentoxide can be advantageously adopted. In the said treatment, there may be used any inert solvent such as water, methylene chloride, chloroform or pyridine depending on the kind of the oxidizing agent. The reaction temperature may be any temperature from cooling with ice to room temperature.

Alternatively, the compound (V: R = alkoxycarbonyl) may be produced by reacting the compound (IV) with dialkyl carbonate in the presence of a basic catalyst such as an alkali metal alkoxide (e.g. sodium methoxide, sodium ethoxide) or an alkali metal hydride (e.g. sodium hydride, lithium hydride) at a temperature from room temperature to refluxing temperature. The said compound (IV) is obtainable by reacting the compound (I) with an α-halopropionic acid derivative of the formula:

in which R and X are each as defined above, followed by hydrolysis and decarboxylation, of which the conversions are representable by the following formulae:

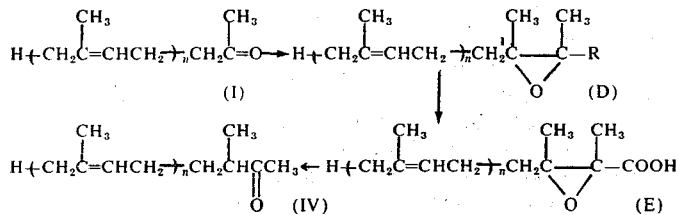

The reaction conditions for the above conversions may be the substantially same as those in the conversions from the compound (I) into the compound (II) through the compounds (A) and (B).

In the fourth step, the thus obtained compound (V) is reacted with the compound (VI), followed by hydrolysis and decarboxylation to give the compound (VIII). The reaction of the compound (V) with the compound (VI) and the subsequent hydrolysis and decarboxylation may be carried out in the same manner as applied in the conversion of the compound (I) to the compound (II). For instance, the reaction of the compound (V) with the compound (VI) in the presence of a basic catalyst in an inert solvent such as a lower alkanol (e.g. methanol, ethanol), followed by hydrolyzing the resultant product with a base in a lower alkanol and decarboxylating the resulting product under an acidic condition, can afford the compound (VIII). When the symbol R' in the compound (VI) is protected hydroxyl, it may be frequently converted into hydroxyl in the course of the above hydrolysis.

In the fifth step, the compound (VIII) is reduced to the compound (IX). The reduction may be carried out in a per se conventional procedure as adopted for the reduction of a carbonyl group. Examples of such procedure are reduction with a metal hydride compound such as lithium aluminum hydride or sodium borohydride, reduction in the presence of an aluminum alkoxide such as aluminum isopropoxide, etc. The reaction is usually carried out in an inert solvent (e.g. methanol, ethanol, ethyl acetate, dioxane) at a wide range of temperature from cooling with ice to refluxing depending on the kind of the reducing agent. When the symbol R' in the compound (VIII) is hydroxyl, it may be protected by reacting previously with an acylating agent (e.g. acetyl chloride, acetic anhydride, benzoyl chloride, mixed anhydride of benzoic acid and sulfuric acid) or an alkylating agent (e.g. diazomethane, methyl bromide, ethyl bromide).

Finally, the thus prepared compound (IX) is subjected to dehydration to give the compound (X). The dehydration may be carried out in the presence of a dehydrating agent (e.g. phosphorous pentoxide, phosphorous oxychloride, sodium hydrogen sulfite, p-toluenesulfonic acid, sulfuric acid, oxalic acid) in an inert solvent (e.g. ether, benzene, toluene, xylene, tetrahydrofuran) at a wide range of temperature from cooling with ice to refluxing.

In each of the steps as above illustrated, the concrete reaction conditions such as reaction time, reaction temperature, reaction pressure, reaction medium and the like may be appropriately decided.

As stated above, the compound (X) obtained by the process of this invention is utilizable as an intermediate in the synthesis of various per se useful polyene compounds such as coezyme Q, vitamin $K_2$ and plastoquinone. For instance, the condensation of the compound (X: R' = OH) with 2,3-dimethoxy-5-methylhydroquinone in the presence of a Lewis acid (e.g. $BF_3$, $AlCl_3$) according to a conventional procedure affords coenzyme Q.

Still, the starting compounds in the process of this invention, i.e. the compound (I) and the compound (VI), are generally known. In particular, the compounds (I) and (VI) are specifically known when $m$ or $n$ is 1 or 2.

Practical and presently preferred embodiments of the present invention are illustratively shown in the following Examples.

EXAMPLE 1

Preparation of farnesylgeranyl acetate

1. Preparation of 2,6,10-trimethyl-5,9-undecadienal:

To a mixture of geranylacetone (171 g) and ethyl monochloroacetate (141 g) at −10°C in the nitrogen stream, sodium ethoxide (71 g) is portionwise added, and the resultant mixture is stirred for 6 hours. A solution of potassium hydroxide (99 g) in methanol (560 ml) is added thereto, and stirring is continued for 2 hours. The reaction mixture is poured into water and skaken with petroleum ether. The water layer is neutralized with acetic acid and extracted with ether. The ether extract is washed with water and dried. After evaporation of the ether, the residual material is distilled under reduced pressure to give 2,6,10-trimethyl-5,9-undecadienal (135 g) as a pale yellow oil. B.P. 100° to 103°C/0.4 mm Hg. Yield, 73.6%. IR: 2680, 1720 cm⁻¹ (CHO).

2. Preparation of ethyl 3,7,11-trimethyl-6,10-dodecadien-2-ol-1-carboxylate:

A suspension of zinc (59 g) in benzene (400 ml) is heated up to the reflux temperature, and a mixture of ethyl bromoacetate (120 g) and 2,6,10-trimethyl-5,9-undecadienal (135 g) is added thereto. The resulting mixture is refluxed for 2 hours, cooled and poured into 5% aqueous solution of sulfuric acid. The benzene layer is washed with water, dried and evaporated. The residual material is distilled under reduced pressure to give ethyl 3,7,11-trimethyl-6,10-dodecadien-2-ol-1-carboxylate (100 g) as a pale yellow oil. B.P. 139° to 142°C/0.08 mm Hg. IR: 3480, 1030 cm⁻¹(OH); 1720, 1180cm⁻¹(COO). NMR (carbon tetrachloride): δ 1.25 (t), 1.58 (s), 1.65 (s), 1.95 (m), 2.38 (m), 4.10 (m), 5.05 (m).

3. Preparation of ethyl 3,7,11-trimethyl-6,10-dodecadien-2-one-1-carboxylate:

To a mixture of pyridine (132 ml) and ethyl 3,7,11-trimethyl-6,10-dodecadien-2-ol-1-carboxylate (132 g), the Cornforth reagent (prepared by adding dropwise a solution of chromium trioxide (223 g) in water (150 ml) to pyridine (2230 ml) while cooling with ice water) is added, and the resultant mixture is allowed to stand at room temperature. After removal of the precipitate by filtration, the reaction mixture is admixed with water and extracted with ether. The ether extract is washed with water, dried and evaporated. The residual material is distilled under reduced pressure to give ethyl 3,7,11-trimethyl-6,10-dodecadien-2-one-1-carboxylate (75 g) as a pale yellow oil. B.P. 125° to 129°C/0.06 mmHg. IR: 1740, 1225 cm⁻¹ (COO); 1710 cm⁻¹ (C=O). NMR (carbon tetrachloride): δ 1.25 (m), 1.61 (s), 1.69 (s), 1.98 (s), 2.0–2.8 (m), 3.33 (s), 4.15 (m), 4.8–5.25 (m).

4. Preparation of 3,7,11,15,19-pentamethyl-2,6,14,18-eicosatetraen-10-on-1-ol:

To a suspension of sodium hydride (2.64 g) in ether (70 ml), a solution of ethyl 3,7,11-trimethyl-6,10-dodecadien-2-one-1-carboxylate (14.7 g) in ether (15 ml) is dropwise added, and then a solution of 1-bromo-8-acetoxy-2,6-dimethyl-2,6-octadiene (15 g) in ether (15 ml) is dropwise added thereto while cooling with ice. The reaction mixture is poured into ice water. The ether layer is washed with water, dried and evaporated. The residue (24.8 g) is added to a solution of potassium hydroxide (8.4 g) in ethanol (150 ml), and the resultant mixture is poured into water, followed by washing with petroleum ether, acidifying with 5% aqueous solution of sulfuric acid and extracting with ether. The ether layer is washed with water, dried and evaporated. The resulting product (23.5 g) is purified by chromatography on silica gel (235 g) using benzene to give 3,7,11,15,19-pentamethyl-2,6,14,18-eicosatetraen-10-on-1-ol (18 g). IR: 3400, 1000 cm⁻¹ (OH): 1705 cm⁻¹ (C=O); 1668 cm⁻¹ (C=C). NMR (carbon tetrachloride): δ 1.04 (d), 1.59 (s), 1.66 (s), 2.01 (m), 2.7 (m), 4.1 (m), 5.05 (m).

5. Preparation of farnesylgeranyl acetate:

a. Preparation of 1-acetoxy-3,7,11,15,19-pentamethyl-2,6,14,18-eicosatetraen-10-ol:

To a mixture of acetic anhydride (8.1 g) and pyridine (3.2 g), 3,7,11,15,19-pentamethyl-2,6,14,18-eicosatetraen-10-on-1-ol (15 g) is added, and stirring is continued while cooling with ice for 3 hours. The reaction mixture is poured into ice water and extracted with ether. The ether extract is washed with water, dired and evaporated to give 1-acetoxy-3,7,11,15,19-pentamethyl-2,6,14,18-eicosatetraen-10-one (15 g). IR: 1740, 1710, 1675 cm⁻¹. NMR (carbon tetrachloride): δ 1.01 (d), 1.56 (s), 1.65 (s), 1.90 (s), 1.97 (s), 2.05–2.71 (m), 4.43 (d), 4.70–5.39 (m).

The above product is dissolved in ethanol (15 ml), and the resultant solution is dropwise added to a solution of sodium borohydride (0.41 g) in ethanol (100 ml) and ethyl acetate (50 ml) while cooling with ice. After stirring for 3 hours, the reaction mixture is poured into ice water and extracted with ether. The ether extract is washed with water, dried and evaporated. The residual product (11 g) is chromatographed on silica gel (110 g) using a mixture of benzene and ethyl acetate (9.5:0.5 by weight). As the fraction (1), 1-acetoxy-3,7,11,15,19-pentamethyl-2,6,14,18-eicosatetraen-10-ol (5.0 g) is obtained. As the fractions (2), 3,7,11,15,19-pentamethyl-2,6,14,18-eicosatetraene-1,10-diol (3.0 g) is obtained.

To a mixture of 3,7,11,15,19-pentamethyl-2,6,14,18-eicosatetraene-1,10-diol (3.75 g) in pyridine (1 ml) while cooling with ice, acetic anhydride (1.53 g) is dropwise added in 15 minutes, and then stirring is continued for 40 minutes. The reaction mixture is poured into ice water and extracted with ether. The ether extract is washed with water, dried and evaporated. The residue (3.9 g) is purified by chromatography on silica gel (40 g) using benzene to give 1-acetoxy-3,7,11,15,19-pentamethyl-2,6,14,18-eicosatetraen-10-ol (3.1 g).

b. Preparation of farnesylgeranyl acetate:

1-Acetoxy-3,7,11,15,19-pentamethyl-2,6,14,18-eicosatetraen-1Q-ol (0.7 g) is dissolved in pyridine (1 ml), and phosphorus oxychloride (0.36 g) is added thereto dropwise while cooling with water. After stirring for 3 hours, stirring is continued at 80°C for 30 minutes, and the reaction mixture is poured into ice water and extracted with ether. The ether extract is washed with water, dried and evaporated. The residual material (0.5 g) is purified by chromatography on silica gel (5 g) using benzene to give farnesylgeranyl acetate (250 mg). IR: 1740, 1230 cm⁻¹ (COO); 1668, 951 cm⁻¹ (C=C). NMR (carbon tetrachloride): δ 1.59 (s), 1.67 (s), 1.96 (s), 2.03 (m), 2.4 (m), 2.75 (m), 4.45 (d), 5.03 (m).

EXAMPLE 2

Preparation of 3,7,11-trimethyl-2,6-dodecadien-10-on-1-ol:

To a suspension of sodium hydride (1.9 g) in ether (40 ml) while cooling with ice, ethyl isobutyroylacetate (5.2 g) is added, and 1-bromo-8-acetoxy-2,6-dimethyl-2,6-octadiene (8 g) is dropwise added thereto. The reaction is carried out with reflux for 8 hours. The ether layer is separated from the reaction mixture, washed with water, dried and evaporated. The oily product (9.9 g) is added to a solution of potassium hydroxide (6.3 g) ethanol (120 g), and refluxing is continued for about 1 hour. The resultant mixture is added to the ice water, made acidic with 10% sulfuric acid and extracted with ether. The ether extract is washed with saturated aqueous solution of sodium chloride, aqueous solution of sodium hydrogen carbonate and water in order, and then the ether is evaporated therefrom. The residue (7.2 g) is dissolved in benzene and purified by chromatography on silica gel to give 3,7,11,-trimethyl-2,6-dodecadien-10-on-1-ol (6.2 g). NMR (carbon tetrachloride): δ 1.05 (d), 1.59 (s), 2.0

(s), 21.–2.7 (m), 3.52 (s), 3.95 (d), 4.8–5.4 (m).

EXAMPLE 3

Preparation of farnesyl acetate

To a solution of 3,7,11-trimethyl-2,6-dodecadien-10-on-1-ol (47.6 g) in acetic anhydride (61 g), pryidine (16 g) is added, and the resultant mixture is allowed to stand while cooling with ice for 3 hours. The reaction mixture is poured on ice and extracted with ether. The ether extract is washed with aqueous saturated solution of sodium chloride, aqueous solution of sodium hydrogen carbonate and water in order, dried over magnesium sulfate and evaporated to give 1-acetoxy-3,7,11-trimethyl-2,6-dodecadien-10-one (53 g) as an oil.

The above product is dropwise added to a solution of sodium borohydride (2.4 g) in ethanol (24 ml) and ethyl acetate (12 ml), and stirring is continued at 15°C for 5 hours. The reaction mixture is poured on ice and extracted with ether. The ether extract is washed as above, dried and evaporated. The residue (48 g) is dissolved in a mixture of benzene (240 ml) and pyridine (40 ml), phosphorus oxychloride (31 g) is dropwise added thereto while cooling with ice and stirring is continued for 3 hours. Then, stirring is further continued at 80°C for 30 minutes. The reaction mixture is poured into ice water and extracted with petroleum ether. The petroleum ether extract is washed as above, dried and evaporated to give farnesyl acetate (40 g). Yield, 71%. IR: 1735 cm$^{-1}$ (COOR); 1675 cm$^{-1}$ (C=C); 1230 cm$^{-1}$ (COC).

EXAMPLE 4

The reactions are carried out as in Example 3 but alternating the order of the acylation and the reduction to give farnesyl acetate. Yield, 81%.

EXAMPLE 5

Preparation of 4,8,12-trimethyl-3,7-tridecadien-11-one-1,1-dicarboxylic acid To a solution of sodium alkoxide in ethanol (prepared from metallic sodium (51 g) and ethanol (760 ml)), ethyl isobutyroylacetate (48 g) is dropwise added while cooling with ice. After stirring for 30 minutes, diethyl 4,8-dimethyl-3,7-nonadien-9-bromo-1,1-dicarboxylate (75 g) is dropwise added to the resulting mixture, and stirring is continued for 2 hours. Then, refluxing is carried out for 8 hours. The reaction mixture is poured into ice water and extracted with ether. The ether extract is washed with water and evaporated. The resulting liquid is distilled under reduced pressure to eliminate a fraction (90 g) boiling at 80°C/4 mmHg. A solution of potassium hydroxide (46 g) in ethanol (874 ml) is added to the residue, and the resultant mixture is refluxed for 3 hours. The reaction mixture is admixed with ice water and shaken with petroleum ether. The water layer is made acidic with 10% sulfuric acid and extracted with ether. The ether extract is washed with water, dried and evaporated to give 4,8,12-trimethyl-3,7-tridecadien-11-one-1,1-dicarboxylic acid (51 g). IR: 1710 cm$^{-1}$ (C=O); 2780 – 2500 cm$^{-1}$ (COOH); 1670 cm$^{-1}$ (C=C).

EXAMPLE 6

Preparation of ethyl 3,7,11-trimethyl-6,10-dodecadien-2-one-1-carboxylate

Into ether (800 ml), 52% paraffin solution of sodium hydride (22.8 g) is suspended, and diethyl carbonate (89.4 g) is portionwise added thereto while cooling with ice in nitrogen stream. Then, 3,7,11-trimethyl-6,10-dodecadien-2-one (88 g) is dropwise added thereto. After refluxing for 15 hours, the reaction mixture is poured into ice water. The ether layer is separated, washed with water, dried and evaporated. The residue is distilled under reduced pressure to give ethyl 3,7,11-trimethyl-6,10-dodecadien-2-one-1-carboxylate (81 g). B.P. 130° to 135°C/0.05 mmHg. IR: 1640, 1675, 1710, 1740 cm$^{-1}$. NMR (carbon tetrachloride): 1.10 (d), 1.29 (t), 1.60 (s), 1.68 (s), 1.98 (s), 2.00–2.80 (broad), 3.33 (s), 4.15 (q), 4.8–5.3 (broad).

EXAMPLE 7

Preparation of solanesyl acetate

1. Preparation of 2,6,10,14,18-pentamethyl-5,9,13,17-nonadecatetraenal

To a mixture of geranylgeranylacetone (32.2 g) and ethyl monochloroacetate (17.2 g), sodium ethoxide (8.85 g) is portionwise added at −10°C in nitrogen stream. The resultant mixture is stirred for 7 hours, a solution of potassium hydroxide (99 g) in methanol (560 ml) is added thereto, stirring is continued for 3 hours and then the resulting mixture is allowed to stand overnight. Then, the reaction mixture is poured into water, washed with petroleum ether, neutralized with acetic acid and extracted with ether. The ether extract is washed with water, dried and evaporated. The residue is heated at 150°C for 30 minutes for decarboxylation. The resulting crude produce (31 g) is purified by chromatography on silica gel (300 g) using benzene to give 2,6,10,14,18-pentamethyl-5,9,13,17-nonadecatetraenal (23.8 g). IR: 2680, 1720 cm$^{-1}$ (CHO).

2. Preparation of ethyl 3,7,11,15,19-pentamethyl-6,10,14,18-eicosatetraen-2-ol-1-carboxylate:

To a mixture of ether (344 ml) and 2,6,10,14,18-pentamethyl-5,9,13,17-nonadecatetraenal (34.4 g), Grignard reagent (prepared by adding portionwise isopropyl bromide (18.5 g) to a mixture of ether (100 ml) and metallic magnesium (3.7 g), adding further t-butyl acetate (17.4 g) thereto while cooling with ice and then stirring the resultant mixture for 1 hour) is dropwise added while cooling with ice. The resultant mixture is stirred at room temperature for 3 hours, and the reaction mixture is poured into an aqueous saturated solution of ammonium chloride. The ether layer is separated, washed with water, dried and evaporated. The residual material is chromatographed on silica gel (500 g) using a mixture of benzene and ethyl acetate (9.5:0.5 by weight) to give ethyl 3,7,11,15,19-pentamethyl-6,10,14,18-eicosatetraen-2-ol-1-carboxylate (28.5 g) as a pale yellow oil. IR: 3480, 1030 cm$^{-1}$ (OH); 1720, 1180 cm$^{-1}$ (COO).

3. Preparation of ethyl 3,7,11,15,19-pentamethyl-6,10,14,18-eicosatetraen-2-one-1-carboxylate:

To a mixture of ethyl 3,7,11,15,19-pentamethyl-6,10,14,18-eicosatetraen-2-ol-1-carboxylate (217 g) and pyridine (215 ml), chromic acid-pyridine (prepared by adding portionwise chromium trioxide (300 g) to a mixture of pyridine (480 ml) and methylene chloride (3000 ml) while cooling with ice) is added thereto, and the resultant mixture is stirred for 4 hours. The reaction mixture is added to water, and the methylene chloride layer is separated, washed with water, dried and evaporated. The residual material (203 g) is chromatographed on silica gel (1kg) using benzene to give ethyl 3,7,11,15,19-pentamethyl-6,10,14,18-eicosatetraen-2-one-1-carboxylate (172 g). IR: 1740, 1225 cm$^{-1}$ (COO); 1710 cm$^{-1}$ (C=O).

4. Preparation of 3,7,11,15,19,23,27,31,35-nonamethyl-2,6,10,14,18,26,30,34-hexatriacontaocta-en-22-on-1-ol:

To a suspension of sodium hydride (2.64 g) in ether (100 ml), a solution of ethyl 3,7,11,15-tetramethyl-6,10,14-hexadecatrien-2-one-1-carboxylate (18.1 g) in ether (18 ml) is dropwise added, and the resulting mixture is dropwise added, and the resulting mixture is stirred for 30 minutes. Then, a solution of 1-bromo-2,6,10,14,18-pentamethyl-20-acetoxy-2,6,10,14,18-eicosapentaene (26 g) in ether (26 ml) is dropwise added thereto. The reaction mixture is poured into ice water. The ether layer is washed with water, dried and evaporated. The residual material is treated as in Example 1 (4) to give 3,7,11,15,19,23,27,31, 35-nonamethyl-2,6,10,14,18,26,30,34-hexatriacontaocta-en-22-on-1-ol (29 g). IR: 3400, 1000 cm$^{-1}$ (OH); 1705 cm$^{-1}$ (C=O); 1668 cm$^{-1}$ (C=C). NMR (carbon tetrachloride): δ 1.59 (s), 1.66 (s), 2.01 (m), 2.7 (m), 4.1 (m), 5.05 (m).

5. Preparation of solanesyl acetate:

a. Preparation of 1-acetoxy-3,7,11,15,19,23,27,31,35-nonamethyl-2,6,10,14,18,26,30,34-hexatriacontaoctaen-22-ol:

To a solution of 3,7,11,15,19,23,27,31,35-nonamethyl-2,6,10,14,18,26,30,34-hexatriacontaocta-en-22-on-1-ol 6.5 g) in pyridine (1 g), acetic anhdyride (3.0 g) is added, and the resulting mixture is allowed to stand at room temperature for 5 hours. The reaction mixture is poured into ice water and shaken with ether. The ether layer is washed with water, dried and evaporated. The residual material (6.5 g) is chromatographed on silica gel (70 g) using benzene to give 1-acetoxy-3,7,11,15,19,23,27,31,35-nonamethyl-2,6,10,14,18,26,30,34-hexatriacontaoctaen-22-one (6.1 g). A solution of this compound in ethanol (6 ml) is dropwise added to a solution of sodium borohydride (0.1 g) in ethanol (10 ml) while cooling with ice, and stirring is continued for 3 hours. The reaction mixture is poured into an aqueous saturated solution of ammonium chloride and extracted with ether. The ether extract is washed with water, dried and concentrated. The residual material (4.8 g) is treated as in Example 1 (5) a) to give 1-acetoxy-3,7,11,15,19,23,27,31, 35-nonamethyl-2,6,10,14,18,26,30,34-hexatriacontaocta-en- 22-ol (2.1 g) as a fraction (1) and 3,7,11,15,19,23,27,31,35-nonamethyl-2,6,10,14,18,26,30,34-hexatriacontaoctaene-1,22-diol (0.9 g) as a fraction (2). The latter is treated with acetic anhydride as above to give 1-acetoxy-3,7,11,15,19,23,27,31,35-nonamethyl-2,6,10,14,18,26,30,34-hexatriacontaoctaen-22-ol (0.82 g).

b. Preparation of solanesyl acetate:

As in Example 1 (5)(b), 1-acetoxy-3,7,11,15,19,23, 27,31,35-nonamethyl-2,6,10,14,18,26,30,34-hexa-triacontaoctaen-22-ol (2.9 g) is treated with phosphorus oxychloride in pyridine to give soranesyl acetate (1.2 g). IR: 1740, 1230 cm$^{-1}$ (C=O); 1668, 951 cm$^{-1}$ (c=C). NMR (carbon tetrachloride): δ 1.58 (s), 1.68 (s), 1.96 (s), 2.03 (m), 2.4 (m), 2.75 (m), 4.45 (d), 5.03 (m).

EXAMPLE 8

Preparation of decaprenyl acetate:

1. Preparation of 3,7,11,15,19,23,27,31,35,39-decamethyl-2,6,10,14,18,26,30,34,38-tetracontanona-en-22-on-1ol:

As in Example 7 (4), ethyl 3,7,11,15,19-pentameth-yl-6,10,14,18-eicosatetraen-2-one-1-carboxylate (4.3 g) and 1-bromo-2,6,10,14,18-pentamethyl-20-acetoxy-2,6,10,14,18-eicosapentaene (4.8 g) are reacted in ether (59 ml) in the presence of sodium hydride (0.26 g). The product is added to a solution of potassium hydroxide (1.68 g) in ethanol (32 ml), and the resultant mixture is treated as in Example 1 (4) to give 3,7,11,15,19,23,27,31,35,39-decamethyl-2,6,10,14,18,26,30,34,38-tetracontanonaen-22-on-1-ol (6.8 g). IR: 3400, 1000 cm$^{-1}$ (OH); 1705 cm$^{-1}$ (C=O); 1668 cm$^{-1}$ (C=C). NMR (carbon tetrachloride): δ 1.59 (s), 1.66 (s), 2.01 (m), 2.7 (m), 4.1 (m), 5.05 (m).

2. Preparation of decaprenyl acetate:

a. Preparation of 1-acetoxy-3,7,11,15,19,23,27,31,35,39-decamethyl-2,6,10,14,18,26,30,34,38-tetracontanonaen-22-ol:

To a solution of 3,7,11,15,19,23,27,31,35,39-decamethyl-2,6,10,14,18,26,30,34,38-tetracontanona-en-22-on-1-ol (6.8 g) in pyridine (1 g), acetic anhydride (3.5 g) is added, and the resultant mixture is allowed to stand at room temperature for 6 hours. The reaction mixture is treated as in Example 7 (5) (a) to give 1-acetoxy-3,7,11,15,19,23,27,31,35,39-decamethyl-2,6,10,14,18,26,30,34,38-tetracontanona-en-22-one (6.2 g), which is then similarly reduced. The resultant product (4.7 g) is treated as in Example 1 (5) (a) to give 1-acetoxy-3,7,11,15,19,23,27,31,35,39-decamethyl-2,6,10,14,18,26,30,34,38-tetracontanona-en-22ol (1.9 g) as a fraction (1) and 3,7,11,15,19,23,27,31,35,39-decamethyl-2,6,10,14,18,26,30,34,38-tetracontanonaene-1,22-diol (0.8 g) as a fraction (2). The latter is treated with acetic anhydride as above to give 1-acetoxy-3,7,11,15,19,23,27,31,35,39-decamethyl-2,6,10,14,18,26,30,34,38-tetracontanonaen-22-ol (0.73 g).

b. Preparation of decaprenyl acetate:

As in Example 1 (5) (b), 1-acetoxy-3,7,11,15,19,23,27,31,35,39-decamethyl-2,6,10,14,18,26,30,34,38-tetracontanonaen-22-ol (2.5 g) is treated with phosphorus oxychloride in pyridine to give decaprenyl acetate (0.98 g). IR: 1740, 1230 cm$^{-1}$ (C=O); 1668, 951 cm$^{-1}$ (C=C). NMR (carbon tetrachloride): δ 1.58 (s), 1.68 (s), 1.96 (s), 2.03 (m), 2.4 (m), 2.75 (m), 4.45 (d), 5.03 (m).

Some of adventageous features of the process of this invention are illustrated below.

1. In the dehydration step for conversion of the compound (IX) into the compound (X), there is formed a double bond. Concerning to such double bond, the production of a cis-isomer and a trans-isomer may be expected. Actually, however, the product in the dehydration step of the process of this invention is all or almost all in a trans form on the said double bond. This is of entirely unexpected nature. Any conventional method could not provide a trans-isomer in a highly predominant proportion, and the process of this invention may be said the first method which can yield a trans-isomer in a satisfactorily predominant proportion in the related art field.

2. When the compound (X) produced in the final step is reacted with an oxidizing agent, for instance, by heating with selenium oxide in a lower alkanol (e.g. ethanol) while refluxing and the resulting product of the formula:

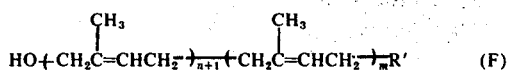 (F)

in which R', $m$ and $n$ are each as defined above is reacted with a halogenating agent, for instance, by treating with phosphorus tribromide or phosphorus trichloride in an inert solvent (e.g. benzene, hexane), preferably in the presence of a basic catalyst (e.g. pyridine) while cooling with ice, there is produced a compound of the formula:

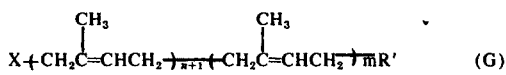 (G)

in which X is halogen and R', $m$ and $n$ are each as defined above. The compound (G) apparently corresponds to the compound (VI) except in the increase of the number of isoprenyl units. Thus, the performance of the process of this invention starting from the compound (VI) to the compound (X) with the said two additional steps can extend the isoprenyl units by the number of $n + 1$. In other words, the compound (X) having an optional number of isoprenyl units is obtainable by the repetition of a series of the steps as above.

3. When the starting compounds, i.e. the compound (I) and the compound (VI), are all in a trans configuration on the double bonds in the isoprenyl units, the repetition of a series of the steps as above can afford the compound (X) having an optional number of isoprenyl units and taking a trans configuration on all the double bonds therein. Since only the polyene compounds having a trans configuration are physiologically and pharmacologically active, the process of this invention is quite useful and valuable.

4. In conventional methods, the isoprenyl unit could be extended only one by one, and the polyene compounds having a long chain have been manufactured only by tendious operations in very low yields. In the process of this invention, the compound (V) wherein $n$ may be any small or large number is reacted with the compound (VI) wherein $m$ may be any small or large number, and thus the polyene compounds having a great number of isoprenyl units can be manufactured in very fewer steps.

What is claimed is:
1. A process for preparing a polyene compound which comprises:
A. reacting a compound of the formula

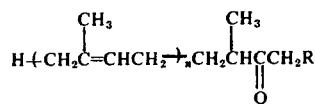

with a compound of the formula

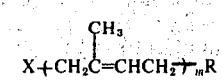

to form a compound of the formula

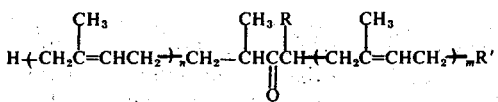

B. subjecting the product of (A) to hydrolysis and decarboxylation to form a compound of the formula

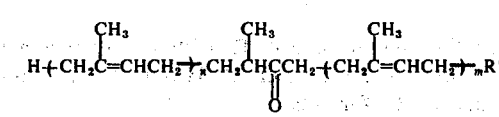

C. reducing the product of (B) to form a compound of the formula

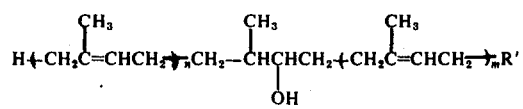

D. reacting the product of (C) with a dehydrating agent to form a compound of the formula

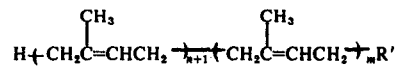

where in each occurence above R is a group convertible into carboxyl on hydrolysis, R' is protected or unprotected hydroxyl or a group of the formula

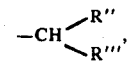

where R'' and R''' are each carboxyl or a group convertible into carboxyl on hydrolysis, X is the residue of an acid, $m$ is a positive integer and $n$ is 0 or a positive integer.

2. A process, as in claim 1, where the reaction (D) is carried out in an inert solvent.

3. A process, as in claim 1, where by dehydrating agent employed in the reaction (D) is a member selected from the group consisting of phosphorus pentoxide, phosphorus oxychloride, sodium hydrogen sulfite, p-toluenesulfonic acid, sulfuric acid and oxalic acid.

4. A process, as in claim 1, where the reduction reaction (C) is carried out by treatment with a metal hydride compound or an aluminum alkoxide in an inert solvent.

5. A process, as in claim 1, where the reaction (A) is carried out in the presence of a basic catalyst in an inert solvent.

6. A process as in claim 1, where the hydrolysis in (B) is carried out by treatment with a base in an inert solvent.

7. A process, as in claim 1, where the decarboxylation in (B) is carried out under acidic conditions.

8. A process, as in claim 1, where the compound reacted in (A) has been formed by:

E. reacting a compound of the formula

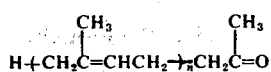

with a carboxylic acid derivative of the formula RCH₂X and subjecting the resultant compound to hydrolysis and decarboxylation to form a compound of the formula

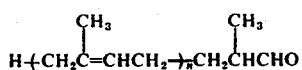

F. reacting the product of (E) with a carboxylic acid derivative of the formula RCH₂X to form a compound of the formula

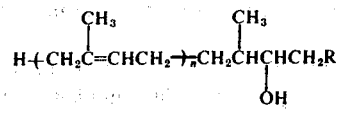

G. reacting the product of (F) with an oxidizing agent, R, X, and $n$ being defined as in claim 1.

9. A process as in claim 1, where the compound reacted in (A) has been formed by E. reacting a compound of the formula

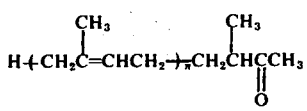

where $n$ is defined in claim 1, with a dialkyl carbonate.

* * * * *